(12) United States Patent
Yoshimi et al.

(10) Patent No.: US 7,663,112 B2
(45) Date of Patent: Feb. 16, 2010

(54) CASSETTE

(75) Inventors: Takuya Yoshimi, Kanagawa (JP); Eiichi Kito, Kanagawa (JP); Tsuyoshi Tanabe, Kanagawa (JP); Takeshi Kuwabara, Kanagawa (JP); Kazuharu Ueta, Tokyo (JP); Makoto Iriuchijima, Gunma (JP); Yasunori Ohta, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 12/219,734

(22) Filed: Jul. 28, 2008

(65) Prior Publication Data

US 2009/0028299 A1 Jan. 29, 2009

(30) Foreign Application Priority Data

Jul. 27, 2007 (JP) ............................. 2007-195624
Jun. 9, 2008 (JP) ............................. 2008-150561

(51) Int. Cl.
*G01T 1/24* (2006.01)

(52) U.S. Cl. ................................. 250/370.08

(58) Field of Classification Search .............. 250/483.1, 250/484.4, 589, 370.08
See application file for complete search history.

(56) References Cited

U.S. PATENT DOCUMENTS

| 5,594,774 | A | * | 1/1997 | Schmidt | ...................... 378/177 |
| 5,844,961 | A | * | 12/1998 | McEvoy et al. | ............ 378/98.8 |
| 2002/0150214 | A1 | * | 10/2002 | Spahn | ....................... 378/189 |
| 2006/0054833 | A1 | * | 3/2006 | Tsuchino et al. | ....... 250/370.11 |

FOREIGN PATENT DOCUMENTS

| JP | 2003-172783 | 6/2003 |
| JP | 2005-003850 | 1/2005 |

* cited by examiner

*Primary Examiner*—David P Porta
*Assistant Examiner*—Mark R Gaworecki
(74) *Attorney, Agent, or Firm*—Jean C. Edwards, Esq.; Akerman Senterfitt

(57) ABSTRACT

A radiation detecting cassette has a casing including a first flat plate for facing a patient and a second flat panel for facing a surgical table. The first flat plate and the second flat panel are spaced from each other by a predetermined distance. The casing also includes a pair of first and second tapered side members disposed on respective side edges of the first and second flat plates. The first and second tapered side members are progressively tapered toward their distal ends. The first and second tapered side members house therein respective radiation shields, which in turn house therein a battery, a cassette controller, and a transceiver.

5 Claims, 9 Drawing Sheets

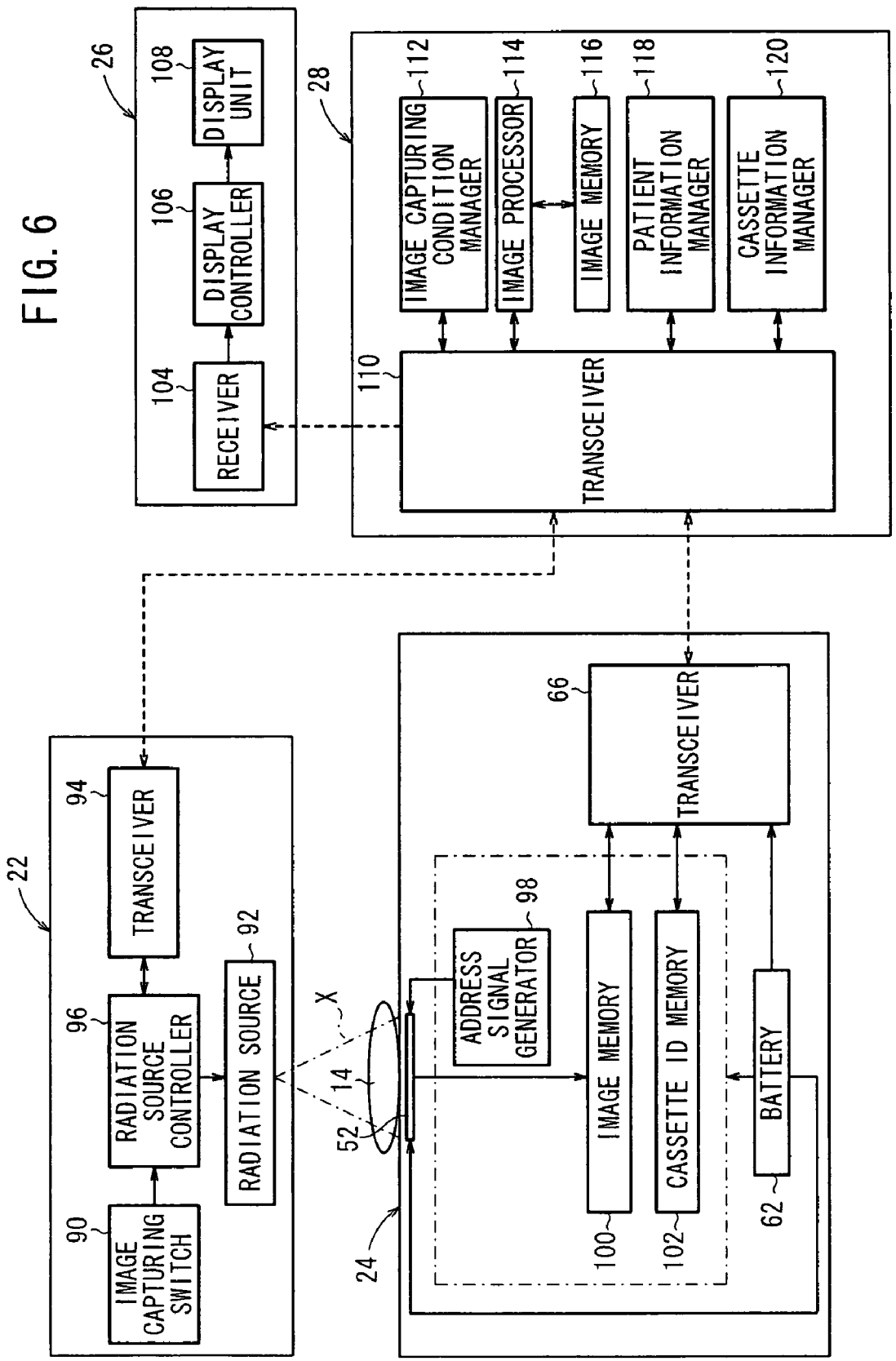

CASSETTE

CROSS-REFERENCE TO RELATED APPLICATIONS

The present application claims priority from Japanese Patent Application Nos. 2007-195624, filed Jul. 27, 2007, and 2008-150561, filed Jun. 9, 2008, the contents of both of which are herein incorporated by reference in their entirety.

BACKGROUND OF THE INVENTION

1. Field of the Invention

The present invention relates to a cassette storing therein a radiation conversion panel for detecting a radiation that has passed through a subject and converting the detected radiation into radiation image information.

2. Description of the Related Art

In the medical field, there have widely been used radiation image capturing apparatus which apply a radiation to a subject and guide the radiation that has passed through the subject to a radiation conversion panel, which captures a radiation image from the radiation. Known forms of the radiation conversion panel include a conventional radiation film for recording a radiation image by way of exposure, and a stimulable phosphor panel for storing a radiation energy representing a radiation image in a phosphor and reproducing the radiation image as stimulated light by applying stimulating light to the phosphor.

The radiation film with the recorded radiation image is supplied to a developing device to develop the radiation, or the stimulable phosphor panel is supplied to a reading device to read the radiation image as a visible image.

In the operating room or the like, it is necessary to read and display a recorded radiation image immediately from a radiation conversion panel after the radiation image is captured for the purpose of quickly and appropriately treating the patient. As a radiation conversion panel which meets such a requirement, there has been developed a radiation detector having a solid-state detector for converting a radiation directly into an electric signal or converting a radiation into visible light with a scintillator and then converting the visible light into an electric signal to read a detected radiation image.

As disclosed in Japanese Laid-Open Patent Publication No. 2003-172783, for example, a radiation conversion panel, a wireless communication mechanism, and a battery are housed in a cassette, and the radiation conversion panel is irradiated with X-rays radiated from a radiation source that is disposed in confronting relation to the image capturing surface of the radiation conversion panel.

The cassette is disposed between a bed and a patient lying on the bed, and placed in a position facing the affected region of the patient for capturing a radiation image of the affected region. Generally, since the cassette is in the form of a thin box and needs to be inserted between the patient and the bed, the cassette that is put in position is physically burdensome to the patient, and cannot easily be placed between the patient and the bed. Accordingly, there have been demands in the art for cassettes that can easily and efficiently be placed in position between the patient and the bed.

SUMMARY OF THE INVENTION

It is a general object of the present invention to provide a cassette which can easily be placed in position between a subject and a bed, can reduce a physical burden imposed on the subject at the time the cassette is placed in position, can efficiently be placed in position, and is small in size.

The above and other objects, features, and advantages of the present invention will become more apparent from the following description when taken in conjunction with the accompanying drawings in which a preferred embodiment of the present invention is shown by way of illustrative example.

BRIEF DESCRIPTION OF THE DRAWINGS

FIG. 6 is a block diagram of the radiation image capturing system shown in FIG. 1;

DESCRIPTION OF THE PREFERRED EMBODIMENT

Figure 1:
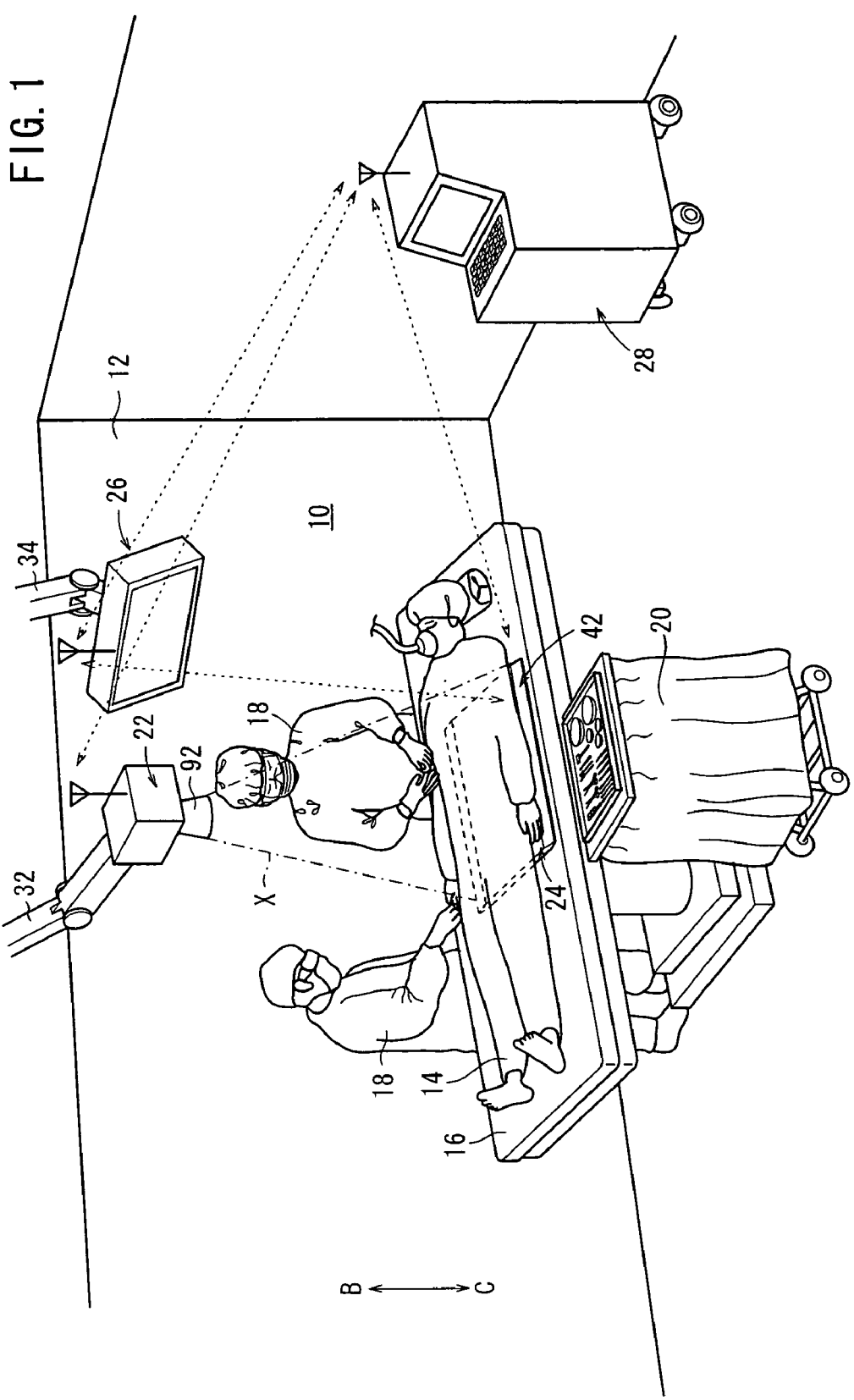
FIG. 1 is a perspective view of an operating room incorporating a radiation image capturing system which employs a radiation detecting cassette according to an embodiment of the present invention.

FIG. 1 shows in perspective an operating room 12 incorporating a radiation image capturing system 10 which employs a radiation detecting cassette 24 according to an embodiment of the present invention. As shown in FIG. 1, the operating room 12 has a surgical table (bed) 16 for a patient (subject) 14 to lie thereon, and an instrument table 20 disposed on one side of the surgical table 16 for placing thereon various tools and instruments to be used by surgeons 18 for operating on the patient 14. The surgical table 16 is surrounded by various apparatus required for surgical operations, including an anesthesia apparatus, an aspirator, an electrocardiograph, a blood pressure monitor, etc.

The radiation image capturing system 10 includes an image capturing apparatus 22 for irradiating the patient 14 with a radiation X at a dose according to image capturing conditions, a radiation detecting cassette 24 housing therein a radiation detector (radiation conversion panel) 52, to be described later, for detecting the radiation X that has passed through the patient 14, a display device 26 for displaying a radiation image based on the radiation X that is detected by the radiation detector 52, and a console 28 for controlling the image capturing apparatus 22, the radiation detecting cassette 24, and the display device 26. The image capturing apparatus 22, the radiation detecting cassette 24, the display device 26, and the console 28 send and receive signals by way of wireless communications.

The image capturing apparatus 22 is coupled to a universal arm 32 so as to be movable to a desired position for capturing a desired area of the patient 14 and also to be retractable to a position out of the way while the surgeons 18 are performing a surgical operation on the patient 14. Similarly, the display device 26 is coupled to a universal arm 34 so as to be movable to a position where the surgeons 18 can easily confirm a captured radiation image displayed on the display device 26.

Figure 2:
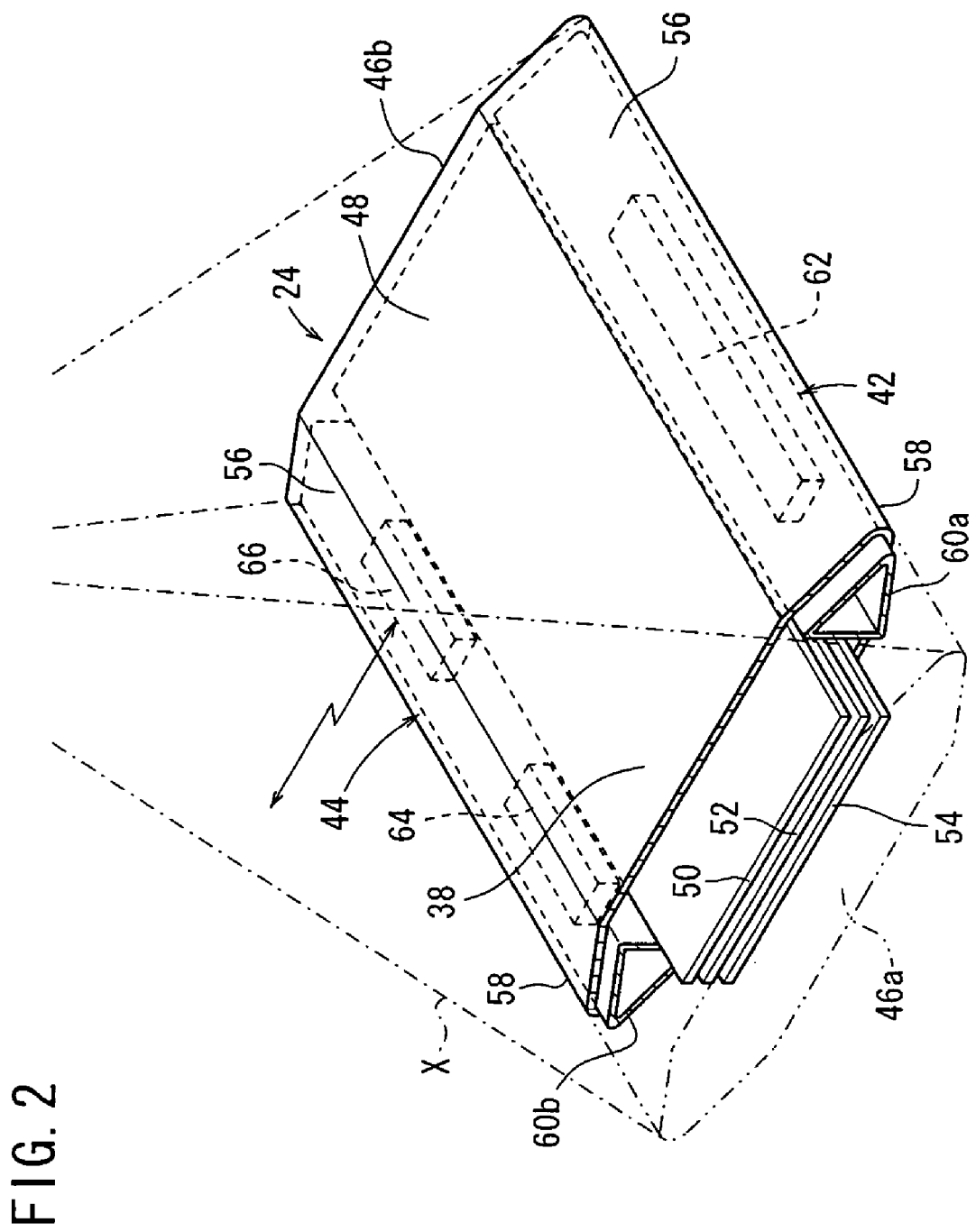
FIG. 2 is a perspective view, partly cut away, showing internal structural details of the radiation detecting cassette.
Figure 3:
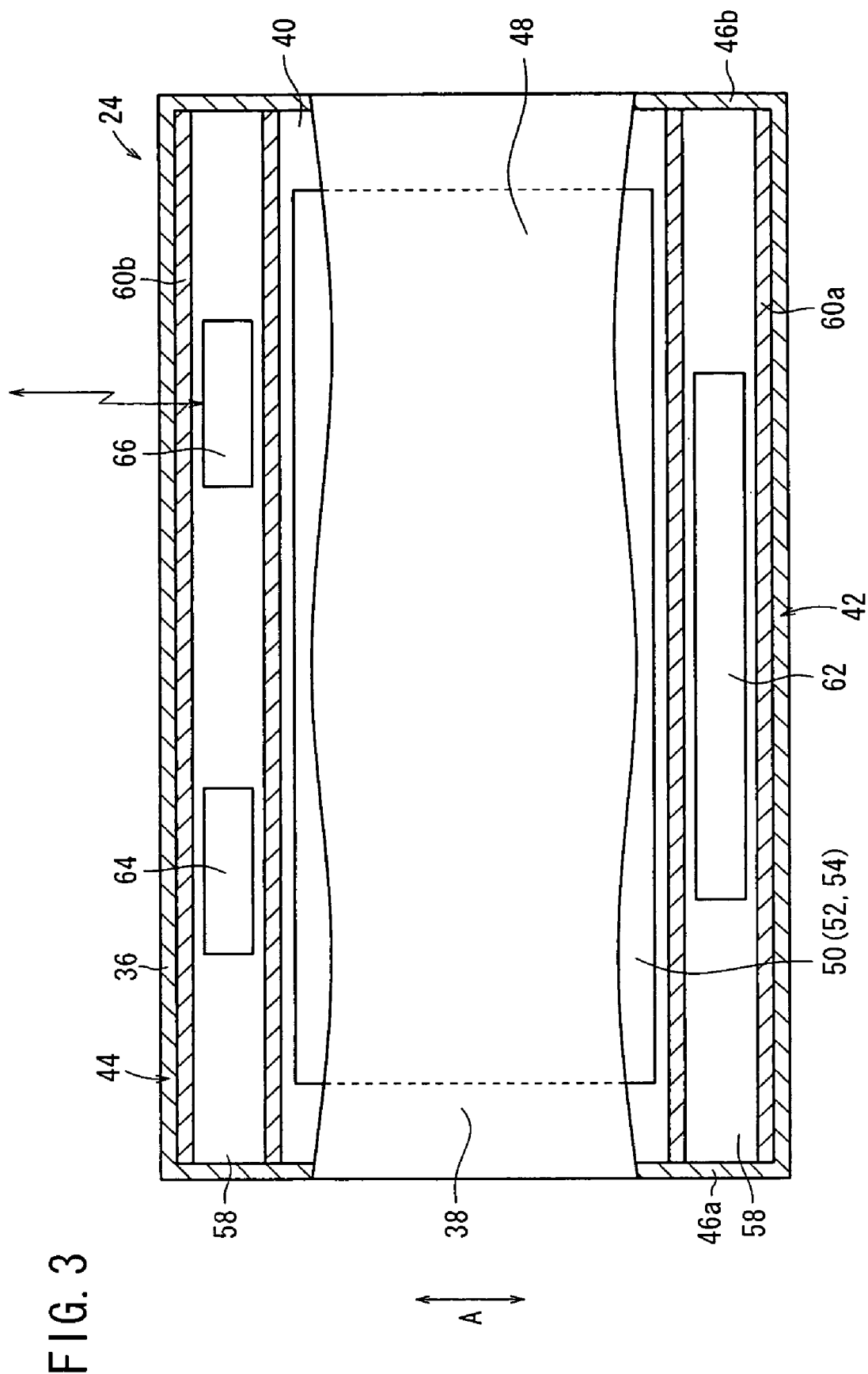
FIG. 3 is a plan view, partly in cross section, of the radiation detecting cassette shown in FIG. 2.
Figure 4:
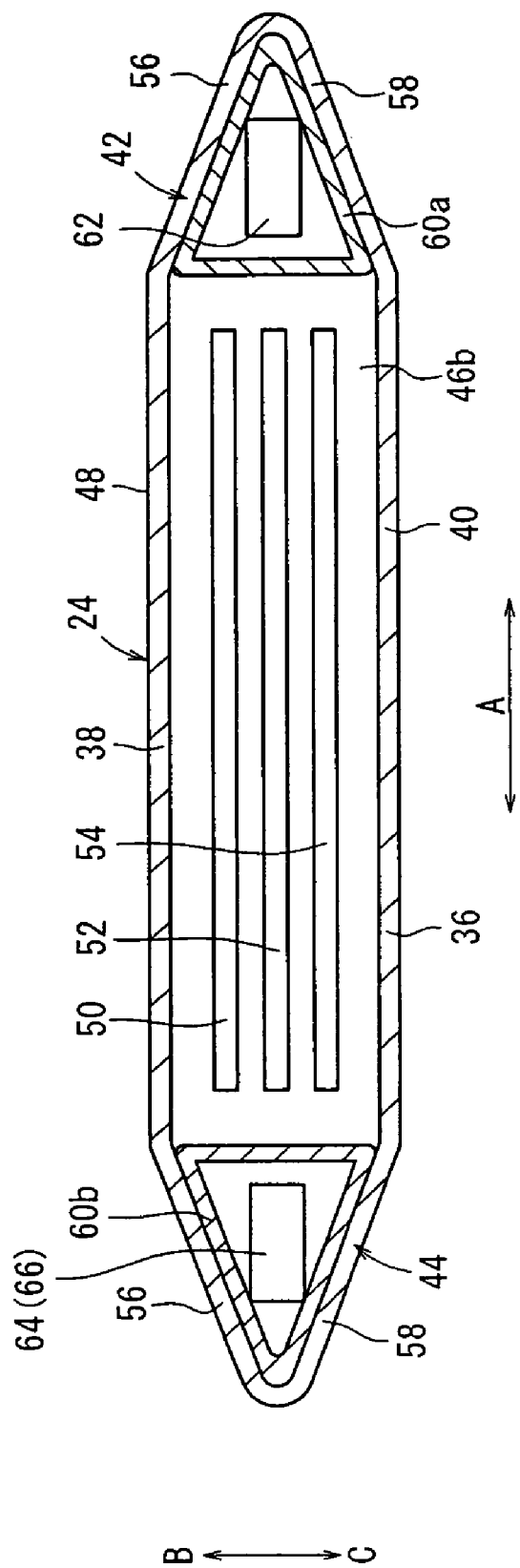
FIG. 4 is a vertical cross-sectional view of the radiation detecting cassette shown in FIG. 2.

FIGS. 2 through 4 show external and internal structural details of the radiation detecting cassette 24.

The radiation detecting cassette 24 includes a casing 36 made of a material that is permeable to the radiation X.

The casing 36 comprises a pair of first and second flat plates 38, 40 of substantially elongate rectangular shape which are spaced a predetermined distance from each other, a pair of first and second tapered side members 42, 44 disposed on and extending along respective longitudinal side edges of the first and second flat plates 38, 40, and a pair of joint walls 46a, 46b extending substantially perpendicularly to the first and second flat plates 38, 40 and the first and second tapered side members 42, 44 and closing the opposite longitudinal ends of the first and second flat plates 38, 40 and the first and second tapered side members 42, 44. When in use, the casing 36 is oriented such that the first flat plate 38 faces the image capturing apparatus 22 and the second flat plate 40 faces the surgical table 16.

The casing 36 houses therein a grid 50 for removing scattered rays of the radiation X from the patient 14, a radiation detector 52 for detecting the radiation X that has passed through the patient 14, and a lead plate 54 for absorbing back scattered rays of the radiation X, which are disposed between the first and second flat plates 38, 40. The grid 50, the radiation detector 52 and the lead plate 54 are successively arranged in that order from a surface 48 of the casing 36 which is irradiated with the radiation X. The irradiated surface 48 of the casing 36 may be constructed as the grid.

The first and second tapered side members 42, 44 are substantially V-shaped in cross section and are progressively tapered toward respective outer distal edges away from the side edges of the first and second flat plates 38, 40.

Each of the first and second tapered side members 42, 44 comprises a first slanted portion 56 joined to the first flat plate 38 and extending downwardly at a predetermined angle away from the first flat plate 38 and a second slanted portion 58 joined to the second flat plate 40 and extending upwardly at a predetermined angle away from the second flat plate 40. The first slanted portion 56 and the second slanted portion 58 have respective outer edges joined to each other at a position that is spaced a predetermined distance from the first and second flat plates 38, 40. The first and second tapered side members 42, 44 are of a symmetrical, cross-sectionally triangular shape in that they are away from each other with the first and second flat plates 38, 40 being positioned therebetween.

Specifically, the casing 36 has a substantially central region in the transverse direction indicated by the arrow A which is perpendicular to the longitudinal direction thereof, the substantially central region being of a constant thickness provided by the first and second flat plates 38, 40, and a pair of opposite transverse edge portions in the transverse direction indicated by the arrow A which are progressively thinner outwardly away from the substantially central region. Stated otherwise, the radiation detecting cassette 24 including the casing 36 is progressively thicker from the opposite transverse edge portions in the transverse direction indicated by the arrow A toward the substantially central region.

The first tapered side member 42 houses therein a hollow tubular radiation shield 60a impermeable to the radiation X which is held against inner wall surfaces thereof. The hollow radiation shield 60a houses therein a battery 62 serving as a power supply for the radiation detecting cassette 24.

Similarly, the second tapered side member 44 houses therein a hollow tubular radiation shield 60b impermeable to the radiation X which is held against inner wall surfaces thereof. The hollow radiation shield 60b houses therein a cassette controller 64 for controlling the radiation detector 52 with electric power supplied from the battery 62, and a transceiver (wireless communication mechanism) 66 for exchanging a signal representing information of the radiation X detected by the radiation detector 52, with the console 28. Each of the radiation shields 60a, 60b is made of a radiation shield sheet of lead, for example. The radiation shields 60a, 60b are of a triangular cross-sectional shape formed along the shape of the first and second tapered side members 42, 44.

Since the tubular radiation shields 60a, 60b are disposed in the respective first and second tapered side members 42, 44, and the battery 62, the cassette controller 64, and the transceiver 66 are housed in the tubular radiation shields 60a, 60b, the battery 62, the cassette controller 64, and the transceiver 66 are protected against damage from the radiation X that is applied to the irradiated surface 48 of the casing 36.

The battery 62, the cassette controller 64, and the transceiver 66 that are housed in the tubular radiation shields 60a, 60b are not limited to being placed in the illustrated positions, but may be positioned otherwise. For example, all the battery 62, the cassette controller 64, and the transceiver 66 may be housed in the first tapered side member 42, or conversely all the battery 62, the cassette controller 64, and the transceiver 66 may be housed in the second tapered side member 44.

The joint walls 46a, 46b are of a flat lozenge shape corresponding to the transverse cross-sectional shape of the casing 36 which is provided by the first and second flat plates 38, 40 and the first and second tapered side members 42, 44.

Figure 5:
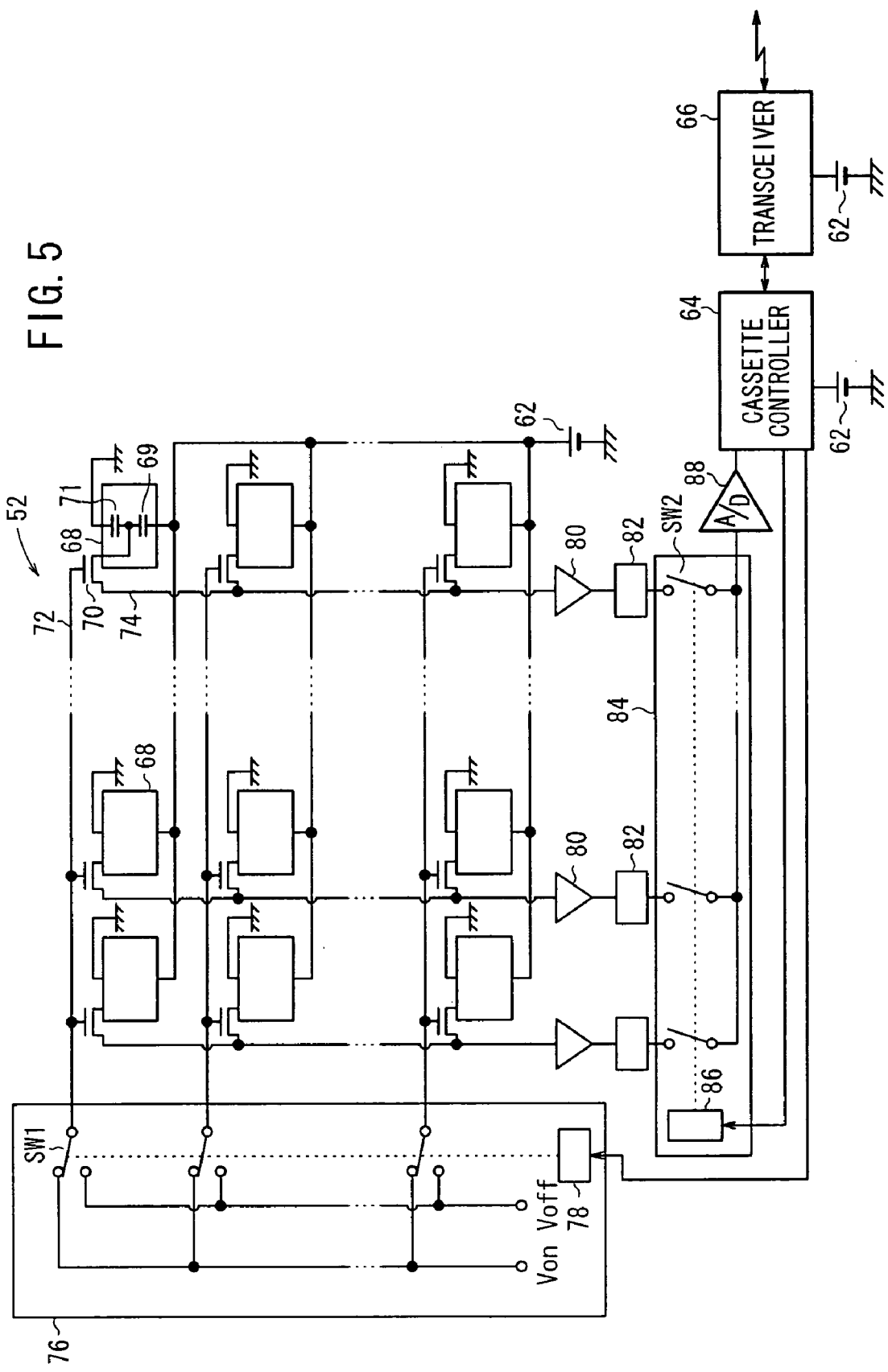
FIG. 5 is a block diagram of a circuit arrangement of a radiation detector of the radiation detecting cassette shown in FIG. 2.

FIG. 5 shows in block form a circuit arrangement of the radiation detector 52. As shown in FIG. 5, the radiation detector 52 comprises an array of thin-film transistors (TFTs) 70 arranged in rows and columns, a photoelectric conversion layer 69 made of a material such as amorphous selenium (a-Se) for generating electric charges upon detection of the radiation X, the photoelectric conversion layer 69 being disposed on the array of TFTs 70, and an array of storage capacitors 71 connected to the photoelectric conversion layer 69. When the radiation X is applied to the radiation detector 52, the photoelectric conversion layer 69 generates electric charges, and the storage capacitors 71 store the generated electric charges. Then, the TFTs 70 are turned on along each row at a time to read the electric charges from the storage capacitors 71 as an image signal. In FIG. 5, the photoelectric conversion layer 69 and one of the storage capacitors 71 are shown as a pixel 68, and the pixel 68 is connected to one of the TFTs 70. Details of the other pixels 68 are omitted from illustration. Since amorphous selenium tends to change its structure and lose its function at high temperatures, it needs to be used in a certain temperature range. Therefore, some mechanism for cooling the radiation detector 52 should preferably be provided in the radiation detecting cassette 24.

The TFTs 70 connected to the respective pixels 68 are connected to respective gate lines 72 extending parallel to the rows and respective signal lines 74 extending parallel to the columns. The gate lines 72 are connected to a line scanning driver 76, and the signal lines 74 are connected to a multiplexer 84 serving as a reading circuit.

The gate lines 72 are supplied with control signals Von, Voff for turning on and off the TFTs 70 along the rows from the line scanning driver 76. The line scanning driver 76 comprises a plurality of switches SW1 for switching between the gate lines 72 and an address decoder 78 for outputting a selection signal for selecting one of the switches SW1 at a time. The address decoder 78 is supplied with an address signal from the cassette controller 64.

The signal lines 74 are supplied with electric charges stored in the storage capacitors 71 of the pixels 68 through the TFTs 70 arranged in the columns. The electric charges supplied to the signal lines 74 are amplified by amplifiers 80 connected respectively to the signal lines 74. The amplifiers 80 are connected through respective sample and hold circuits 82 to the multiplexer 84. The multiplexer 84 comprises a plurality of switches SW2 for successively switching between the signal lines 74 and an address decoder 86 for outputting a selection signal for selecting one of the switches SW2 at a time. The address decoder 86 is supplied with an address signal from the cassette controller 64. The multiplexer 84 has an output terminal connected to an A/D converter 88. A radiation image signal generated by the multiplexer 84 based on the electric charges from the sample and hold circuits 82 is converted by the A/D converter 88 into a digital image signal representing radiation image information, which is supplied to the cassette controller 64.

FIG. 6 shows in block form the radiation image capturing system 10 which comprises the image capturing apparatus 22, the radiation detecting cassette 24, the display device 26, and the console 28.

The image capturing apparatus 22 comprises an image capturing switch 90, a radiation source 92 for outputting the radiation X, a transceiver 94 for receiving image capturing conditions from the console 28 by way of wireless communications and transmitting an image capturing completion signal, etc. to the console 28 by way of wireless communications, and a radiation source controller 96 for controlling the radiation source 92 based on an image capturing start signal supplied from the image capturing switch 90 and image capturing conditions supplied from the transceiver 94.

The radiation detecting cassette 24 houses therein the radiation detector 52, the battery 62, the cassette controller 64, and the transceiver 66.

The cassette controller 64 comprises an address signal generator 98 for supplying address signals to the address decoder 78 of the line scanning driver 76 and the address decoder 86 of the multiplexer 84 of the radiation detector 52, an image memory 100 for storing the radiation image information detected by the radiation detector 52, and a cassette ID memory 102 for storing cassette ID information for identifying the radiation detecting cassette 24.

The transceiver 66 receives a transmission request signal from the console 28 by way of wireless communications and transmits the cassette ID information stored in the cassette ID memory 102 and the radiation image information stored in the image memory 100 to the console 28 by way of wireless communications.

The display device 26 comprises a receiver 104 for receiving the radiation image information from the console 28, a display controller 106 for controlling the display of the received radiation image information, and a display unit 108 for displaying the radiation image information processed by the display controller 106.

The console 28 comprises a transceiver 110 for transmitting and receiving necessary information including radiation image information, positional information, etc. to and from the image capturing apparatus 22, the radiation detecting cassette 24, and the display device 26 by way of wireless communications, an image capturing condition manager 112 for managing image capturing conditions required for the image capturing apparatus 22 to capture radiation images, an image processor 114 for processing radiation image information transmitted from the radiation detecting cassette 24, an image memory 116 for storing the radiation image information processed by the image processor 114, a patient information manager 118 for managing patient information of the patient 14 whose images are to be captured, and a cassette information manager 120 for managing cassette information transmitted from the radiation detecting cassette 24.

The console 28 may be located outside of the operating room 12 insofar as it can transmit and receive signals to and from the image capturing apparatus 22, the radiation detecting cassette 24, and the display device 26 by way of wireless communications.

The radiation image capturing system 10 which employs the radiation detecting cassette 24 according to the present embodiment is basically constructed as described above, and operation of the radiation image capturing system 10 will be described below.

The radiation image capturing system 10 is installed in the operating room 12 and used when a radiation image of the patient 14 is required by the surgeons 18 who are performing an operation on the patient 14. Before a radiation image of the patient 14 is captured, patient information of the patient 14 to be imaged is registered in the patient information manager 118 of the console 28. If an area to be imaged of the patient 14 and an image capturing method have already been known, they are registered as image capturing conditions in the image capturing condition manager 112. After the above preparatory process is finished, the surgeons 18 perform an operation on the patient 14.

For capturing a radiation image of the patient 14 during the operation, one of the surgeons 18 or the radiological technician places the radiation detecting cassette 24 in a given position between the patient 14 and the surgical table 16 with the first flat plate 38 of the casing 36 facing the image capturing apparatus 22 and the patient 14 (in the direction indicated by the arrow B) and with the second flat plate 40 facing the surgical table 16 (in the direction indicated by the arrow C) (see FIG. 4).

Figure 7A:
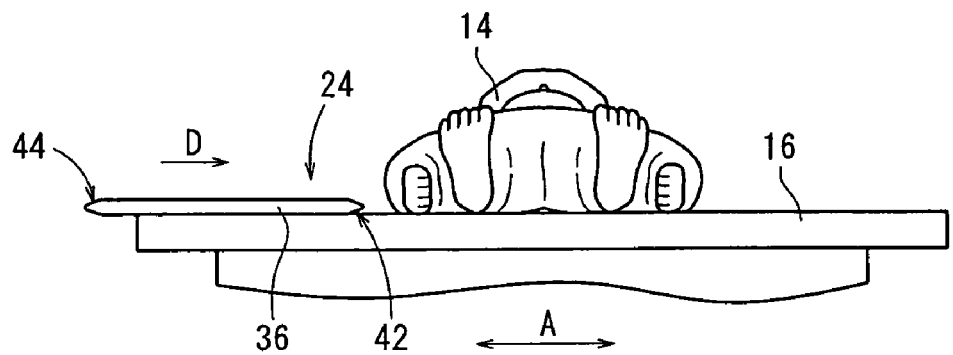
FIGS. 7A through 7C are end elevational views illustrative of a process of placing the radiation detecting cassette between a patient and a surgical table.
Figure 7B:
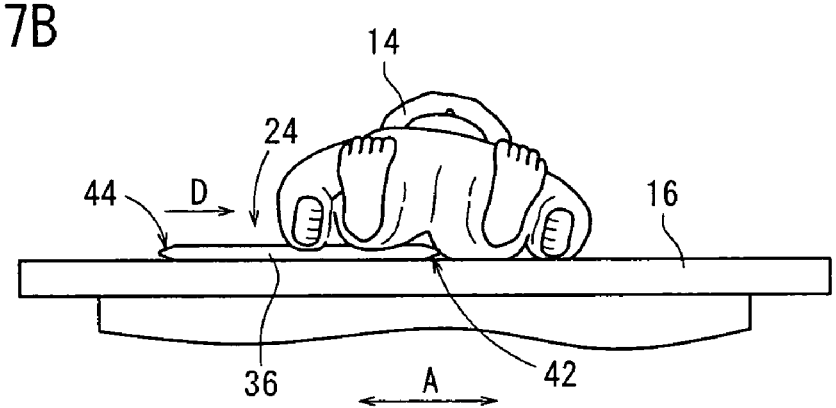
Figure 7C:
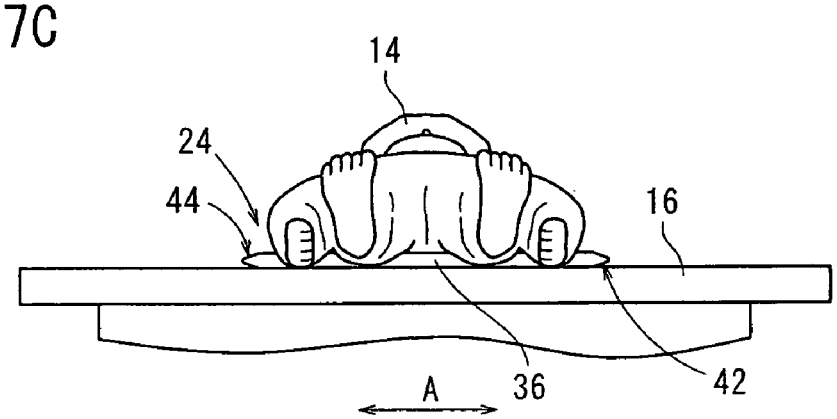

A process of placing the radiation detecting cassette 24 will briefly be described below with reference to FIGS. 7A through 7C. In FIGS. 7A through 7C, the patient 14 lying on the surgical bed 16 in the operating room 12 is viewed in end elevation from its feet.

First, as shown in FIG. 7A, the radiation detecting cassette 24 is placed on the surgical bed 16 on one side of the patient 14 such that the first tapered side member 42 of the casing 36 faces a predetermined position between the patient 14 and the surgical bed 16. At this time, the side edge of the radiation detecting cassette 24 which includes the first tapered side member 42 lies substantially parallel to the patient 14. Then, the radiation detecting cassette 24 is pushed toward the patient 14 in the direction indicated by the arrow D. As the radiation detecting cassette 24 is displaced, the first tapered side member 42 is brought into contact with the side of the patient 14. Thereafter, as shown in FIG. 7B, the radiation detecting cassette 24 is moved toward the predetermined position between the patient 14 and the surgical bed 16, while the first and second slanted portions 56, 58 are being forcibly wedged between the patient 14 and the surgical bed 16, pushing the patient 14 upwardly from the surgical bed 16.

Since the patient 14 is gradually lifted from the surgical table 16 by the first tapered side member 42 whose thickness is progressively reduced toward the outer edge thereof (see FIG. 7B), the patient 14 suffers a less physical burden and the radiation detecting cassette 24 is placed more easily in position between the patient 14 and the surgical table 16 than if the radiation detecting cassette has no tapered side member 42.

Then, the radiation detecting cassette 24 is further pushed toward the patient 14 in the direction indicated by the arrow D until the first flat plate 38 is positioned beneath the patient 14, placing the radiation detecting cassette 24 in the predetermined position between the patient 14 and the surgical bed 16 (see FIG. 7C).

The radiation detecting cassette 24 can also be placed into the predetermined position between the patient 14 and the surgical bed 16 in the same manner as described above when the second tapered side member 44 is forcibly wedged between the patient 14 and the surgical bed 16.

After the radiation detecting cassette 24 is installed in the predetermined position between the patient 14 and the surgical bed 16, the image capturing switch 90 is turned on to capture a radiation image of the patient 14.

The radiation source controller 96 of the image capturing apparatus 22 requests the console 28 to transmit the image capturing conditions from the image capturing condition manager 112 via the transceivers 94, 110. Based on the request, the console 28 transmits the image capturing conditions about the area to be imaged of the patient 14 to the image capturing apparatus 22 via the transceivers 94, 110. When the radiation source controller 96 receives the image capturing conditions, it controls the radiation source 92 to apply a radiation X at a given dose to the patient 14 according to the image capturing conditions.

The radiation X which has passed through the patient 14 is applied to the grid 50, which removes scattered rays of the radiation X. Then, the radiation X is applied to the radiation detector 52, and converted into electric signals by the photoelectric conversion layer 69 of the pixels 68 of the radiation detector 52. The electric signals are stored as electric charges in the storage capacitors 71 (see FIG. 5). The stored electric charges, which represent radiation image information of the patient 14, are read from the storage capacitors 71 according to address signals which are supplied from the address signal generator 98 of the cassette controller 64 to the line scanning driver 76 and the multiplexer 84.

Specifically, in response to the address signal supplied from the address signal generator 98, the address decoder 78 of the line scanning driver 76 outputs a selection signal to select one of the switches SW1, which supplies the control signal Von to the gates of the TFTs 70 connected to the gate line 72 corresponding to the selected switch SW1. In response to the address signal supplied from the address signal generator 98, the address decoder 86 of the multiplexer 84 outputs a selection signal to successively turn on the switches SW2 to switch between the signal lines 74 for thereby reading the electric charges stored in the storage capacitors 71 of the pixels 68 connected to the selected gate line 72, through the signal lines 74.

The electric charges read from the storage capacitors 71 of the pixels 68 connected to the selected gate line 72 are amplified by the respective amplifiers 80, sampled by the sample and hold circuits 82, and supplied to the multiplexer 84. Based on the supplied electric charges, the multiplexer 84 generates and supplies a radiation image signal to the A/D converter 88, which converts the radiation image signal into a digital signal. The digital signal which represents the radiation image information is stored in the image memory 100 of the cassette controller 64.

Similarly, the address decoder 78 of the line scanning driver 76 successively turns on the switches SW1 to switch between the gate lines 72 according to the address signal supplied from the address signal generator 98. The electric charges stored in the storage capacitors 71 of the pixels 68 connected to the successively selected gate lines 72 are read through the signal lines 74, and processed by the multiplexer 84 and the A/D converter 88 into digital signals, which are stored in the image memory 100 of the cassette controller 64.

The radiation image information represented by the digital signals stored in the image memory 100 is transmitted through the transceiver 66 to the console 28 by way of wireless communications.

The radiation image information transmitted to the console 28 is received by the transceiver 110, processed by the image processor 114, and then stored in the image memory 116 in association with the patient information of the patient 14 registered in the patient information manager 118.

The radiation image information processed by the image processor 114 is transmitted from the transceiver 110 to the display device 26. In the display device 26, the receiver 104 receives the radiation image information, and the display controller 106 controls the display unit 108 to display a radiation image based on the radiation image information. The surgeons 18 perform the operation on the patient 14 while visually confirming the radiation image displayed on the display unit 108.

Since no cables for transmitting and receiving signals are connected between the radiation detecting cassette 24 and the console 28, between the image capturing apparatus 22 and the console 28, and between the console 28 and the display device 26, no such cables are placed on the floor of the operating room 12 and hence there are no cable-induced obstacles to the operation performed by the surgeons 18, the radiological technician, or other staff members in the operating room 12.

The casing 36 is not limited to the above structure which includes the first and second tapered side members 42, 44 along the longitudinal side edges of the casing 36. Instead, the casing 36 may additionally have tapered end members that are progressively tapered toward outer distal edges thereof, on the respective longitudinal ends where the joint walls 46a, 46b are disposed. In other words, the casing 36 may have tapered members on the respective four sides thereof. If the casing 36 has tapered members on the respective four sides thereof, then the radiation detecting cassette 24 can easily be displaced in the longitudinal direction of the patient 14 and placed in a desired position between the patient 14 and the surgical bed 16 without imposing an undue physical burden on the patient 14.

According to the present embodiment, as described above, the casing 36 housing the radiation detector 52 therein has the first and second tapered side members 42, 44 progressively tapered toward the respective outer distal edges thereof, and the battery 62, the cassette controller 64, and the transceiver 66 are housed in the first and second tapered side members 42, 44. The casing 36 also includes the radiation shields 60a, 60b. The first and second tapered side members 42, 44 are disposed on the respective side edges of the casing 36 which will not face the patient 14 and the surgical table 16 when the radiation detecting cassette 24 is installed between the patient 14 and the surgical table 16.

The first and second tapered side members 42, 44 allow the radiation detecting cassette 24 to be inserted progressively between the patient 14 and the surgical table 16. Consequently, the radiation detecting cassette 24 can easily and efficiently be installed in position between the patient 14 and the surgical table 16 without imposing an undue physical burden on the patient 14.

Inasmuch as the battery 62, the cassette controller 64, and the transceiver 66 are housed in the first and second tapered side members 42, 44, the space in the casing 36 is effectively utilized, preventing the casing 36 from increasing in size due to the first and second tapered side members 42, 44. As a result, the radiation detecting cassette 24 including the casing 36 is relatively small in size.

When the radiation detecting cassette 24 is used in the operating room 12 or the like, the radiation detecting cassette 24 may be subjected to adhesion of blood, contamination, etc. However, when the radiation detecting cassette 24 is designed to have a waterproof and hermetically-sealed structure, and is sterilized and cleaned as necessary, one radiation detecting cassette 24 can be used repeatedly.

The radiation detecting cassette 24 is not limited to use in the operating room 12, and may be used for a medical examination and a round in the hospital.

Also, the radiation detecting cassette 24 may communicate with external devices via optical wireless communication using infrared light or the like, instead of general wireless communication using radio wave.

Figure 8:
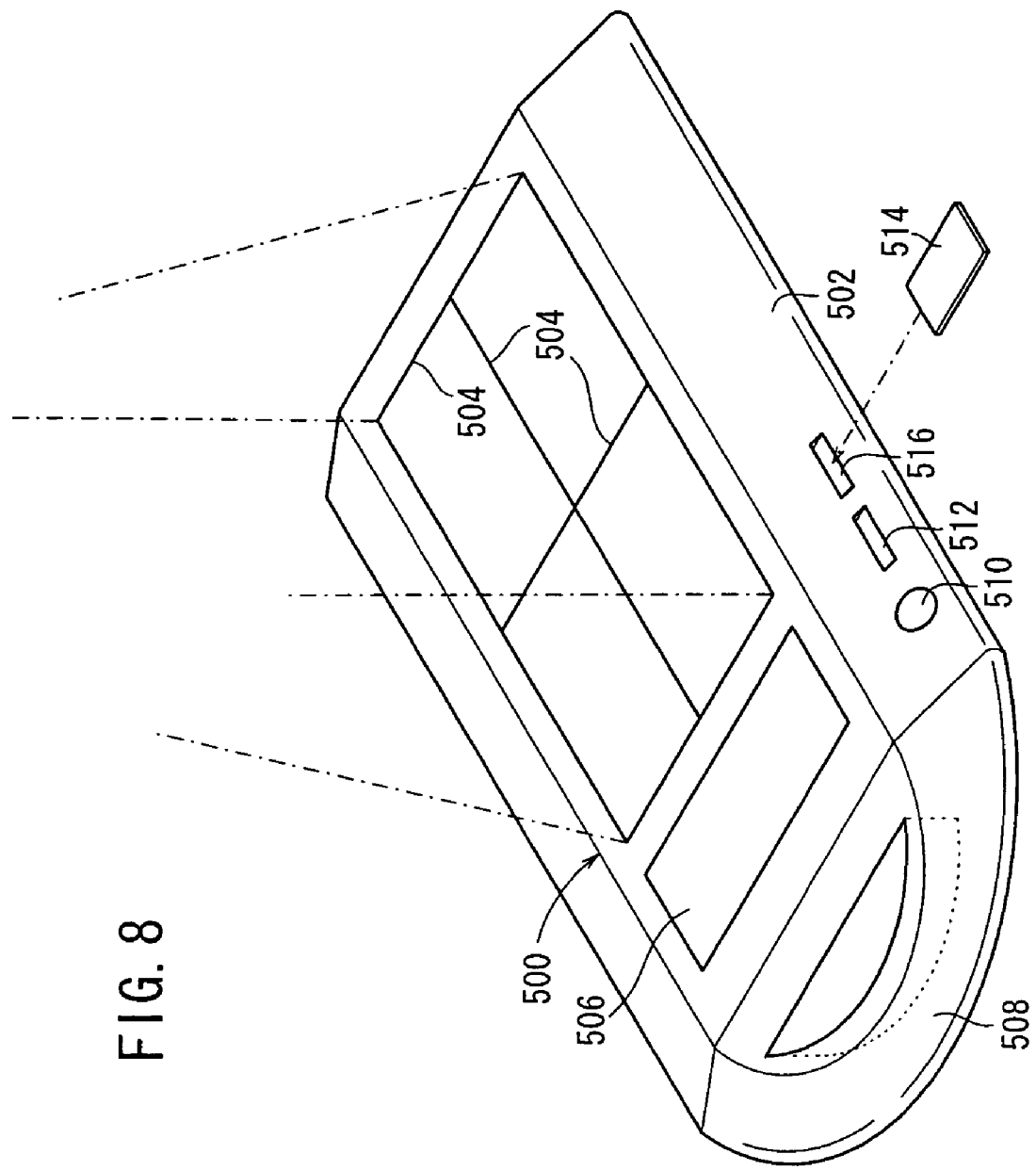
FIG. 8 is a perspective view showing another radiation detecting cassette used in the radiation image capturing system.

Preferably, the radiation detecting cassette 500 may be constructed as shown in FIG. 8.

Specifically, the radiation detecting cassette 500 includes a guiding line 504 drawn on the radiation-irradiated surface of a casing 502, the guiding line 504 serving as a reference for setting a captured area and a captured position. Using the guiding line 504, a subject can be positioned with respect to the radiation detecting cassette 500, and an area irradiated with the radiation can be set, thereby recording radiation image information on an appropriate captured area.

The radiation detecting cassette 500 is provided with a display section 506 on an area thereof other than the captured area, for displaying various information about the radiation detecting cassette 500. The information which is displayed on the display section 506, includes ID information of a subject whose radiation image information is to be recorded on the radiation detecting cassette 500, the number of times the radiation detecting cassette 500 has been used, an accumulated exposed radiation dose, a charging state (remaining battery level) of a battery 62 in the radiation detecting cassette 500, image capturing conditions of radiation image information, and a positioning image of the subject with respect to the radiation detecting cassette 500. In this case, a technician confirms a subject based on the ID information displayed on the display section 506, for example, and also previously confirms that the radiation detecting cassette 500 is placed in a usable state. Then, the technician positions a desired captured area of the subject with respect to the radiation detecting cassette 500 based on the displayed positioning image, thereby capturing appropriate radiation image information.

Also, the radiation detecting cassette 500 is provided with a handgrip 508, whereby it is easier to handle and carry the radiation detecting cassette 500.

Preferably, the radiation detecting cassette 500 may have, on a side thereof, an input terminal 510 for an AC adapter, a USB (Universal Serial Bus) terminal 512, and a card slot 516 for inserting a memory card 514.

When the charging function of the battery 62 in the radiation detecting cassette 500 becomes deteriorated, or when there is not enough time to fully charge the battery 62, the input terminal 510 is connected to the AC adapter to externally supply the radiation detecting cassette 500 with electric power, thereby enabling the radiation detecting cassette 500 to be used immediately.

The USB terminal 512 or the card slot 516 may be used when the radiation detecting cassette 500 cannot transmit and receive information to and from external devices such as the console 28 via wireless communication. Specifically, by connecting a cable to the USB terminal 512, the radiation detecting cassette 500 can transmit and receive information to and from the external devices via wire communication. Alternatively, the memory card 514 is inserted into the card slot 516, and necessary information is recorded on the memory card 514. After that, the memory card 514 is removed from the card slot 516, and the memory card 514 is inserted into the external device, thereby enabling information to be transferred.

Figure 9:
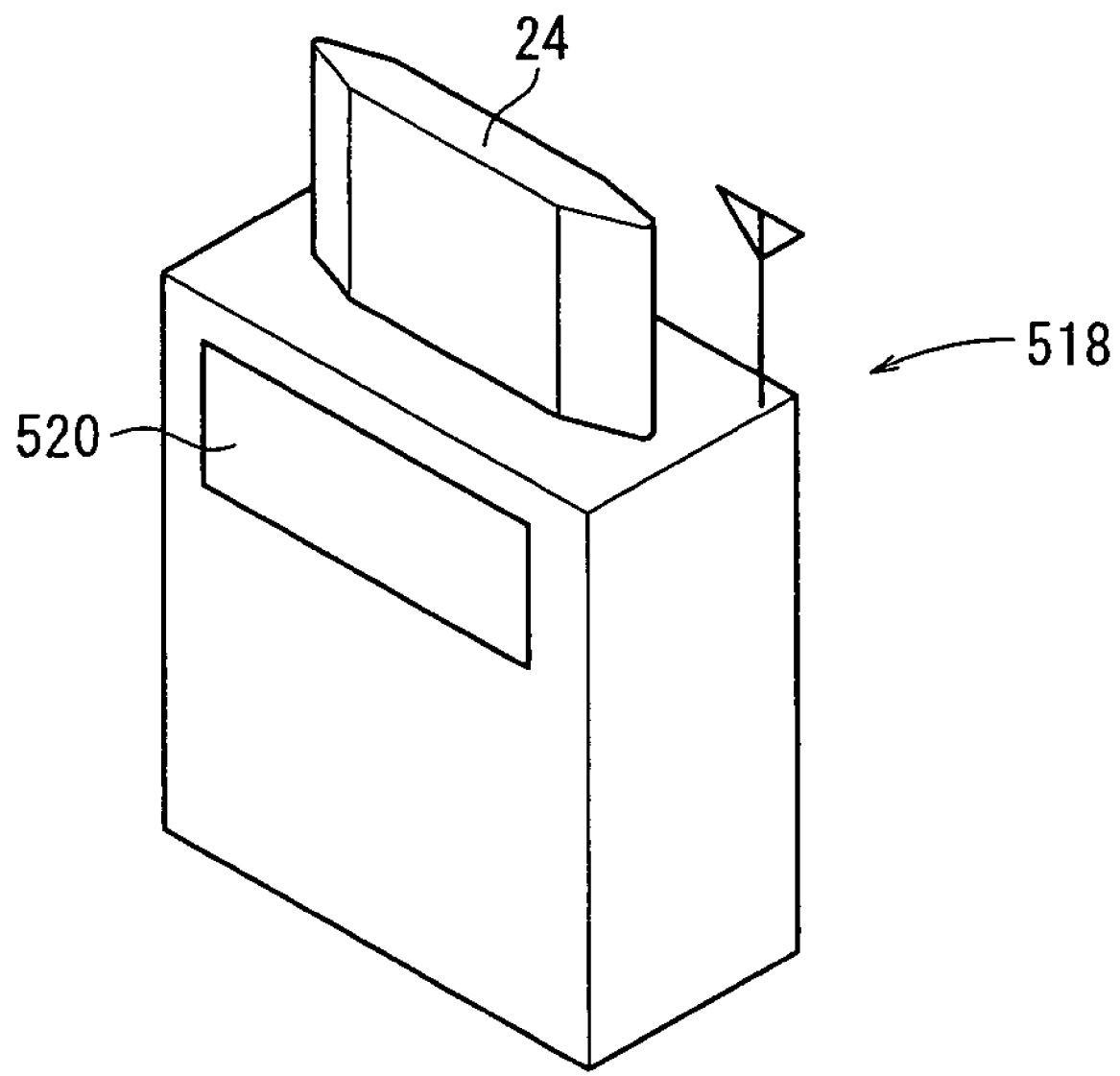
FIG. 9 is a perspective view showing a cradle which charges the radiation detecting cassette.

Preferably, a cradle 518 may be disposed in the operating room 12 or at a desired place in the hospital, into which the radiation detecting cassette 24 is inserted to charge the internal battery 62, as shown in FIG. 9. In this case, in addition to charging the battery 62, the cradle 518 may transmit and receive necessary information to and from external devices such as HIS, RIS, the console 28, etc. by way of wireless or wire communications of the cradle 518. The information may include radiation image information which is recorded on the radiation detecting cassette 24 inserted into the cradle 518.

Also, the cradle 518 may be provided with a display section 520. The display section 520 may display necessary information including a charging state of the inserted radiation detecting cassette 24 and radiation image information acquired from the radiation detecting cassette 24.

Further, a plurality of cradles 518 may be connected to a network. In this case, information about charging states of radiation detecting cassettes 24 inserted in respective cradles 518 can be collected through the network, and the radiation detecting cassette 24 in a usable state can be located.

Although a certain preferred embodiment of the present invention has been shown and described in detail, it should be understood that various changes and modifications may be made therein without departing from the scope of the appended claims.

What is claimed is:

1. A cassette comprising:
    a casing housing therein a radiation conversion panel for detecting a radiation emitted from a radiation source and having passed through a subject and converting the detected radiation into radiation image information;
    a tapered member disposed on said casing and progressively tapered toward an end thereof
    said tapered member being disposed on a side edge of said casing which does not face the subject and a bed on which the subject lies, when said casing is placed between said subject and said bed;
    a wireless communication mechanism for performing wireless communications with an external device, said wireless communication mechanism being disposed in said tapered member; and
    a radiation shield impermeable to said radiation, said radiation shield being housed in said tapered member, said wireless communication mechanism being disposed in said radiation shield,
    wherein said radiation shield is hollow and triangle-shaped in cross section formed along the shape of the cross section of said tapered member.

2. A cassette according to claim 1, further comprising a battery for energizing said radiation conversion panel and said wireless communication mechanism, said battery being disposed in said tapered member.

3. A cassette according to claim 1, further comprising a cassette controller for controlling said radiation conversion panel, said cassette controller being disposed in said tapered member.

4. A cassette according to claim 1, wherein said tapered member comprises a pair of tapered members disposed on respective side edges of said casing, and
    each of said tapered members is V-shaped in cross section.

5. A cassette according to claim 1, wherein said casing comprises a pair of flat plates disposed between said tapered members, said radiation conversion panel being housed between said flat plates.

* * * * *